United States Patent [19]
Wells

[11] Patent Number: 4,490,985
[45] Date of Patent: Jan. 1, 1985

[54] METHOD OF DEHYDRATING NATURAL GAS

[75] Inventor: Richard E. Wells, Tulsa, Okla.

[73] Assignee: General Signal Corporation, Stamford, Conn.

[21] Appl. No.: 509,138

[22] Filed: Jun. 29, 1983

[51] Int. Cl.$^3$ ............................................. F25B 9/00
[52] U.S. Cl. ........................................ 62/86; 62/93; 62/402
[58] Field of Search .......................... 62/93, 402, 86

[56] References Cited

U.S. PATENT DOCUMENTS

| | | |
|---|---|---|
| 625,126 | 5/1899 | Smith . |
| 2,193,209 | 3/1940 | Sandberg . |
| 2,214,368 | 9/1940 | Greensfelder et al. . |
| 2,528,028 | 10/1950 | Barry . |
| 2,586,002 | 2/1952 | Carson, Jr. et al. . |
| 2,786,802 | 3/1957 | Hanisian et al. . |
| 2,937,503 | 5/1960 | Swearingen et al. . |
| 3,226,948 | 1/1966 | Alderson et al. ........... 62/93 |
| 3,541,802 | 11/1970 | Swearingen . |
| 3,587,243 | 6/1971 | Keller ................... 62/93 |
| 3,765,168 | 10/1973 | Wagle . |
| 3,854,300 | 12/1974 | Gerhold . |
| 4,132,535 | 1/1979 | Rivers, Jr. et al. . |
| 4,169,506 | 10/1979 | Berry . |

OTHER PUBLICATIONS

"Turboexpanders and Processes That Use Them," reprinted from *Chemical Engineering Progress*, Jul., 1972, J. S. Swearingen, pp. 95–102.

"Turboexpanders and Expansion Processes for Industrial Gases," J. S. Swearingen, pp. 36–42.

"Engineer's Guide to Turboexpanders," reprinted from *Hydrocarbon Processing*, Apr., 1970, J. S. Swearingen.

*Primary Examiner*—Ronald C. Capossela
*Attorney, Agent, or Firm*—Barnes & Thornburg

[57] ABSTRACT

A method for dehydration of natural gas is provided wherein well head gas is supplied to a three-phase inlet separator, the vapor mixture of natural gas and water removed from that inlet separator means is supplied to a turboexpander, and the resulting refrigerated mixture of natural gas and condensed water vapor is supplied to a multi-phase outlet separator. The turboexpander may have integral means for subsequent compression of the refrigerated mixture and may be coupled through reduction gears to a means for generating electricity. A portion of the refrigerated mixture may be connected to a heat exchanger for cooling the well head natural gas prior to entry into the inlet separator. The flow of refrigerated mixture to this heat exchanger may be controlled by a temperature sensitive valve downstream of the heat exchanger. Methanol may be injected into the vapor mixture prior to entry into the turboexpander. The flow of methanol into the vapor mixture may be controlled by a valve sensitive to the flow rate of the vapor mixture and the water vapor content of the refrigerated mixture. Natural gas vapor from the outlet separator may be recirculated through the turboexpander if the output water vapor content of the natural gas vapor stream is too high.

14 Claims, 1 Drawing Figure

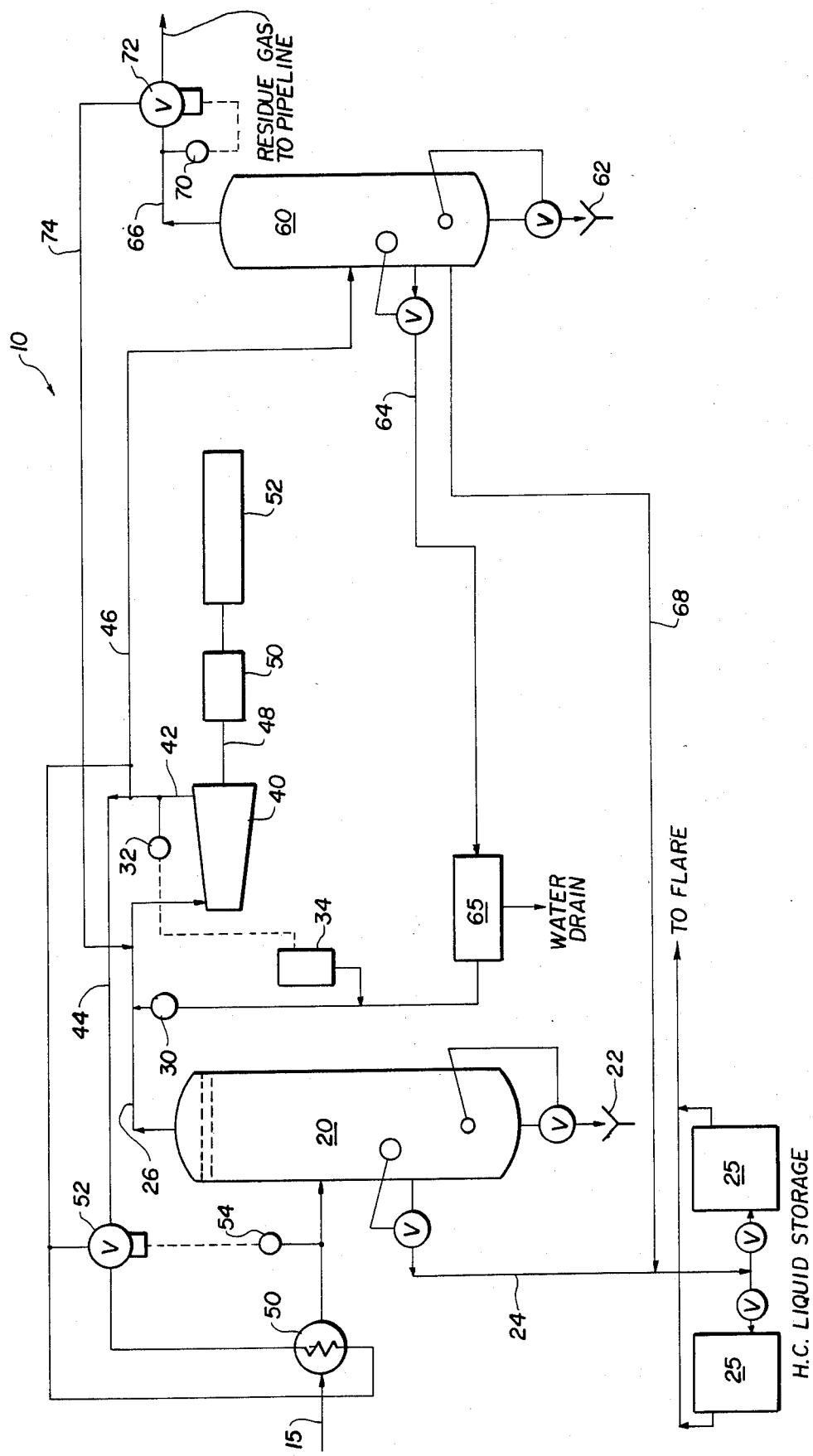

METHOD OF DEHYDRATING NATURAL GAS

BACKGROUND OF THE INVENTION

The present invention relates generally to methods for dehydrating natural gas streams in order to control the formation of hydrates in downstream gas lines. More particularly, the present invention is concerned with a method for dehydrating natural gas with low temperature refrigeration by isentropic expansion of the gas stream.

Dehydration is the process for removing water vapor from the gas stream. Water vapor is an undesirable impurity in natural gas for several reasons. When cooled below its dewpoint, water vapor condenses to liquid water which will itself accelerate corrosion and reduce gas transmission efficiency through elements in the natural gas pipelines and plant equipment. Also, quantities of $H_2S$ and $CO_2$ may be entrained in water particles and, thus, cause further corrosion problems. Finally, liquid water and water vapor can combine with low molecular weight hydrocarbons to form solid, crystalline hydrates which plug valves, fittings, and gas lines. Dehydration devices are typically employed at the well head, and on offshore platforms it is especially important that equipment be explosion proof and as compact as possible.

Problems caused by entrained water in gas lines are well known in the prior art, and several control techniques have been suggested. These methods include refrigeration, absorption, and centrifugal separating or "scrubbing". Unfortunately, prior art devices utilizing these methods are typically very large, expensive, and require multiple moving parts and auxiliarly energy sources.

Refrigeration dehydration devices typically employ isothermal processes with natural gas streams and, thus, require large coolant reservoirs or bulky heat exchangers and electrically powered compressors. These elements take up much space in the limited confines of an offshore rig and increase the risk of explosion from stray electrical voltages and failure of moving compressor elements. Further, prior refrigeration methods often cause water to freeze out in solid form. Electrical or gas heating means are often then required to melt the water to liquid form for removal.

Absorption dehydration, while presently one of the most commercially favored methods, requires extremely complicated processing systems. Water vapor is removed from the natural gas stream by absorption into a hydroscopic liquid, typically triethylene glycol (TEG). Water vapor and some hydrocarbons are so absorbed as they flow through a series of bubble cap trays in a contactor means. Rich, or water ladden, TEG then passes through several filtering and regeneration stages to remove the water and entrained hydrocarbons. Often, several pumping stages are also needed before the lean TEG is returned to the contactor means. Thus, this method also requires a large amount of space. Further, the risk of explosion is increased since not only are there many moving mechanical elements subject to failure, the TEG regeneration stages may require electrical or gas heating means.

Centrifugal scrubbing separates water from natural gas by taking advantage of the difference in their densities. While this may be accomplished by relatively compact machinery, as compared to absorption devices, it often requires extremely high speed, electrically powered rotors to centrifugally separate out the water. Again, stray electrical voltages and rotor failure present a significant risk of explosion.

Thus, the need has arisen for a compact and relatively explosion-proof means of dehydrating well head natural gas. It is of course also desirable that such a dehydration means be inexpensive, mechanically simple, and have a low operating cost. Further, since the natural gas producing industry as a whole has shown inertia and reluctance to implement new production techniques, any such improved dehydration means must have proven or readily apparent reliability.

While it is known to use a turboexpander means in conjuction with the processing of hydrocarbons and natural gas, the purpose and effect of the subject invention are not taught. Turboexpanders have been used where light hydrocarbons are recycled and stockpiled as refrigerants in systems concerned with separating out various liquid hydrocarbons of different temperatures of vaporization. Extremely low temperatures are required, and the light hydrocarbons change phase several times as they are intermixed and separated from diverse fluids.

SUMMARY OF THE INVENTION

An object of the present invention is to provide an improved method and apparatus for dehydration of gases.

Another object of the present invention is the provision of a compact and relatively explosion-proof means for dehydrating natural gas streams.

A further object of the present invention is to provide a reliable dehydration means for well head natural gas streams which requires no auxiliarly energy source.

Still another object is the provision of an inexpensive means of removing water vapor from natural gas using isentropic expansion to produce refrigeration without freezing and which may be employed to generate additional electrical energy.

These and other objects of the present invention are met in the provision of a method for dehydration of natural gas is provided wherein well head natural gas is supplied to a three-phase inlet separator means, the vapor mixture of natural gas and water removed from that inlet separator means is supplied to turboexpander means, and the resulting refrigerated mixture of natural gas and condensed water vapor is supplied to a multiphase outlet separator means. The inlet and outlet separator means permit liquids, particulate solids, and gas vapor to be drawn off separately. The turboexpander means provides low temperature refrigeration by isentropic expansion to condense the water vapor in the vapor mixture to a liquid. The turboexpander means may have integral means for subsequent compression of the refrigerated mixture and may be coupled through reduction gears to a means for generating electricity.

A portion of the refrigerated mixture may be connected to a heat exchanger means for cooling the well head natural gas prior to entry into the inlet separator means. The flow of refrigerated mixture to this heat exchanger means may be controlled by temperature sensitive valve means downstream of the heat exchanger means. Methanol may be injected into the vapor mixture prior to entry into the turboexpander means. The flow of methanol into the vapor mixture may be controlled by valve means sensitive to the flow rate of the vapor mixture and the water vapor content of the refrigerated mixture. Natural gas vapor from the outlet separator means may be recirculated through the turboexpander means if the output water vapor content of the natural gas stream is too high.

Other objects, advantages, and novel features of the present invention will be readily apparent to those skilled in the art when the following detailed description of a preferred embodiment is considered in conjunction with the accompanying drawing.

BRIEF DESCRIPTION OF THE DRAWING

The FIGURE shows a schematic diagram of a natural gas dehydration means according to the present invention.

DESCRIPTION OF THE PREFERRED EMBODIMENTS

The FIGURE, which illustrates a preferred embodiment of the present invention, shows natural gas dehydration means 10 having inlet separator means 20, turboexpander means 40, and outlet separator means 60. Fluids are supplied to inlet separator means 20 by conduit 15. Since it is especially advantageous to initiate natural gas dehydration in the proximity of the well head, fluid input to inlet separator means 20 may include natural gas vapor, water vapor, liquid water and hydrocarbons, and some particulate matter. Inlet separator means 20 may be a multiphase device, as is commonly known and presently used in the industry. Thus, water particulate matter may be drained off by conduit 22, and liquid hydrocarbons may be withdrawn by conduit 24. These drawn off liquid hydrocarbons may be carried by conduit 24 to storage tanks 25 for further processing or to be burned off.

Natural gas and water in a vapor mixture may be drawn off from the top of inlet separator 20 by conduit 26. This vapor mixture, which may also contain some residual hydrocarbons, is then supplied to the input of turboexpander means 40. Turboexpander means 40 is a means for producing low temperature refrigeration by isentropic expansion. Since many such suitable devices are presently commercially available, details of turboexpander structure and operation will not be discussed in detail herein. The particular capacities and operational features may be selected so as to achieve desired temperatures, pressures, and flow rates for a given embodiment. For the purposes of the present invention, it has been found to be desirable that turboexpander means 40 reduce the temperature and pressure of the vapor mixture gas stream so that water vapor condenses out to a liquid state while natural gas remains a vapor. This may be done, for example, by reducing the temperature to 33° Farenheit and the pressure to one atmosphere. Since the water vapor is not frozen out of the vapor mixture, the present invention does not require either additional heating means to melt the water or for turboexpander means 40 to be shut down in order to remove the frozen water from turboexpander means 40. Likewise, at such temperatures and pressures residual hydrocarbon vapors may also be condensed out to a liquid state. However, it is important to note that the natural gas remains in a vaporous state. To facilitate the flow of the refrigerated mixture of natural gas vapor and liquid water condensed from the water vapor out of turboexpander means 40 through conduit 42, turboexpander means 40 may advantageously be provided with an integral compressor stage after the water vapor condensing stage. Again, such devices are presently commercially available and will, thus, not be discussed in detail herein.

Since the composition of the fluid stream and its flow rate into inlet separator means 20 from the well head is typically variable, at any given time the water vapor content of the vapor mixture may be more or less than the capacity of a given turboexpander means 40 to condense out at a given flow rate. While excess water content may be readily removed by providing a larger turboexpander means with a greater capacity, it is often desirable to provide as compact a dehydration unit as possible. It may therefore be advantageous in a particular operating environment to include methanol injection means 30 connected to conduit 26. Methanol functions similarly to TEG in serving to absorb water vapor in the vapor mixture flowing through conduit 26. Turboexpander means 40 may further be advantageously used to condense out water-rich methanol vapor to a liquid state at the same time that pure water vapor is condensed out to a liquid state. As the refrigerated mixture of liquid water, liquid rich methanol, and natural gas vapor passes through conduit 42, sensor means 32 may be employed to detect flow rate and the residual water vapor content of the natural gas vapor. If this water vapor content exceeds a predetermined level per unit volume of natural gas vapor, sensor 32 provides a signal to methanol injection control means 34. Control means 34 will then cause the amount of methanol injected into conduit 26 to increase. Likewise, if the water vapor content per unit volume of natural gas in conduit 42 is too low, control means 34 will cause a decrease in the amount of injected methanol. Alternatively, methanol may be injected into the vapor mixture to prevent freezing of the condensed water vapor in conduit 42.

Well head fluid streams typically reach the surface having high temperatures. It may, in particular operating environments, be desirable to cool this gas stream to cause condensation of some water, undesirable hydrocarbons, and aromatic compounds to liquid states prior to supplying this fluid stream to inlet separator means 20. This may be easily and efficiently accomplished with the present invention. Conduit 42 may be branched to conduits 44 and 46. Conduit 44 will carry a portion of the refrigerated mixture to heat exchanger means 50, in contact with conduit 15 carrying the well head fluids. The volume of the refrigerated mixture carried through conduit 44 and, thus, the cooling capacity of heat exchanger means 50 is controlled by cutoff valve means 52. Valve means 52 may be responsive to temperature sensor means 54, disposed downstream of heat exchanger means 50. Thus, if the temperature of the well head fluid stream entering inlet separator 20 is too high, valve means 52 may be opened to provide greater flow of the refrigerated mixture to heat exchanger means 50 to lower the well head fluid stream temperature. Similarly, valve means 52 may be closed if the well head fluid stream is too cool.

After passing through heat exchanger means 50, the refrigerated mixture is warmed and returns along conduit 44 to join conduit 46, thus raising the temperature of the refrigerated mixture flowing directly from conduit 42 to conduit 46. This may prove advantageous where the external operating environment could otherwise cause the liquid water to freeze in conduit 46 and reduce fluid flow therethrough.

Another feature of the present invention is that, not only are auxiliary energy sources not required, turboexpander means 40 may be coupled by axle 48 to reduction gear means 50 and generator means 52. Thus, electrical energy may be produced by the water vapor condensation process.

The refrigerated mixture continues along conduit 46, supplying fluid to outlet separator means 60. Outlet separator means 60 may resemble inlet separator means 20 in that it may be a multi-phase device which separates out various liquids and gases. Again, such devices are presently commercially available and will not be discussed in detail herein. Various capacities and specific operating characteristics may be selected to satisfy particular operational requirements. With respect to the present invention, outlet separator 60 should permit the natural gas vapor to be withdrawn separately from the liquid water and hydrocarbons (and liquid rich methanol, if that feature is employed). Liquid water may be drained by conduit 62. If methanol injection is employed, liquid methanol may be withdrawn by conduit 64 and supplied to methanol regeneration means 65. Regeneration means 65 removes the water entrained in the methanol and supplies the resulting lean methanol injection means 30. Such regeneration means are presently commercially available and will not be discussed in detail herein. Conduit 68 is provided to withdraw any other liquid hydrocarbons that were condensed out of the vapor mixture by turboexpander means 40. As with the liquid hydrocarbons in conduit 24, these may be supplied to storage tanks 25.

Natural gas vapor may be withdrawn from outlet separator means 60 by output conduit 66. In current natural gas production, commercial grade natural gas must have a guaranteed maximum water vapor content, for example, seven pounds per million cubic feet of natural gas. Flow rate and water vapor sensor means 70 is provided in conduit 66 to determine if the output gas stream is within such predetermined production limits. If the residual water vapor content of the output natural gas exceeds these limits, bypass valve means 72 may be actuated to cause the natural gas vapor in conduit 66 to be recycled through conduit 74 to turboexpander means 40.

The overall structure of the present invention is thus extremely compact and requires only a fraction of the space needed by a TEG dehydrator. Further, the present invention requires no auxiliary energy source, produces significantly less noise and vibration than prior art devices, and has increased structural integrity. Since only the turboexpander has moving parts and even those are minimal, the possibility of mechanical failure and explosion are significantly reduced. Still further, the control system necessary for operation of the present natural gas dehydration unit is greatly simplified. Thus, the present invention provides a more reliable and efficient replacement for bulky prior art systems.

Although the present invention has been described above in detail, the same is by way of illustration and example only, and is not to be taken as a limitation. Those skilled in the art will readily recognize that many possible variations are within the spirit of the present invention. The spirit and scope of the present invention are to be limited only by the terms of the appended claims.

What is claimed is:

1. A method for dehydration of well head natural gas comprising:
   supplying said well head natural gas to a multi-phase inlet separation means for removing hydrocarbon liquids and liquid water therefrom;
   supplying a vapor mixture of natural gas containing water vapor from said inlet separator means to turboexpander means for low temperature refrigeration by isentropic expansion to condense out said water vapor from said vapor mixture of natural gas to create a fluid, refrigerated mixture therefrom; and
   supplying said refrigerated mixture of natural gas vapor and condensed water vapor to a multiphase outlet separator means for removing said condensed water vapor from said natural gas.

2. The method for dehydration of well head natural gas according to claim 1, wherein said refrigerated mixture of natural gas and condensed water vapor is compressed prior to delivery to said outlet separator.

3. The method for dehydration of well head natural gas according to claim 2, wherein said turboexpander means includes means for compressing said refrigerated mixture of natural gas and condensed water vapor integral therewith.

4. The method for dehydration of well head natural gas according to claim 1, wherein the method includes maintaining refrigeration temperature of said mixture of natural gas and water vapor within said turbo expander means is not less than 33° F. at one atmosphere of pressure so that while said water vapor condenses to a liquid state, it is not frozen to a solid.

5. The method for dehydration of well head natural gas according to claim 1, wherein said refrigerated mixture of natural gas and condensed water vapor is supplied to heat exchanger means for cooling said well head natural gas prior to delivery to said inlet separator means.

6. The method for dehydration of well head natural gas according to claim 1, further including supplying methanol to said vapor mixture of natural gas and water prior to entry to said turboexpander means.

7. The method for dehydration of well head natural gas according to claim 1, further including supplying said natural gas from said outlet separator means to said turboexpander means for further condensation of water vapor remaining in said natural gas.

8. An apparatus for treating and dehydrating natural gas comprising:
   multi-phase inlet separator means having input means for receiving well head natural gas, means for removing liquified water and hydrocarbons from a well head natural gas stream, and means for outputting a vapor mixture of natural gas and water vapor;
   turboexpander means having input means for receiving said vapor mixture, means for lowering the temperature and pressure of said vapor mixture to condense out said water vapor, and means for outputting a refrigerated mixture of natural gas vapor and condensed water vapor; and
   multi-phase outlet separator means having input means for receiving said refrigerated mixture, means for removing liquified water and hydrocarbons from said refrigerated mixture, and means for outputting natural gas vapor.

9. The apparatus for treating and dehydrating natural gas according to claim 8, wherein means are provided for inputting said natural gas output from said outlet separator means to said turboexpander means for further condensation of water vapor entained therein.

10. A method for dehydration of well head natural gas comprising:

supplying said well head natural gas to a multi-phase inlet separation means for removing hydrocarbon liquids and liquid water therefrom;

supplying a vapor mixture of natural gas containing water vapor from said inlet separator means to turboexpander means for low temperature refrigeration by isentropic expansion to condense out said water vapor from said vapor mixture of natural gas to create a fluid, refrigerated mixture therefrom;

supplying said refrigerated mixture of natural gas vapor and condensed water vapor to heat exchanger means for cooling said well head natural gas prior to delivery to said inlet separator means, wherein the flow of said refrigerated mixture of natural gas and condensed water vapor to said heat exchanger means is controlled by valved means responsive to the temperature of said well head natural gas downstream of said heat exchanger means; and supplying said refrigerated mixture of natural gas vapor and condensed water vapor to a multiphase outlet separator means for removing said condensed water vapor from said natural gas.

11. A method for dehydration of well head natural gas comprising:

supplying said well head natural gas to a multi-phase inlet separation means for removing hydrocarbon liquids and liquid water therefrom;

supplying a vapor mixture of natural gas containing water vapor from said inlet separator means to turboexpander means for low temperature refrigeration by isentropic expansion to condense out said water vapor from said vapor mixture of natural gas to create a fluid, refrigerated mixture therefrom;

supplying said refrigerated mixture of natural gas vapor and condensed water vapor to a multiphase outlet separator means for removing said condensed water vapor from said natural gas; and further supplying methanol to said vapor mixture of natural gas and water prior to entry to said turboexpander means, the flow of said methanol to said vapor mixture being controlled by valved means responsive to the temperature of said refrigerated mixture of natural gas and condensed water vapor so as to prevent freezing of said condensed water vapor.

12. The method for dehydration of well head natural gas according to claim 11, wherein said methanol applied to said mixture of natural gas and water vapor is reclaimed from said refrigerated mixture of natural gas and condensed water vapor, regenerated to remove entrained water and hydrocarbons, and resupplied to said vapor mixture of natural gas and water.

13. A method for dehydration of well head natural gas comprising:

supplying said well head natural gas to a multi-phase inlet separation means for removing hydrocarbon liquids and liquid water therefrom;

supplying a vapor mixture of natural gas containing water vapor from said inlet separator means to turboexpander means for low temperature refrigeration by isentropic expansion to condense out said water vapor from said vapor mixture of natural gas to create a fluid, refrigerated mixture therefrom;

supplying said refrigerated mixture of natural gas vapor and condensed water vapor to a multiphase outlet separator means for removing said condensed water vapor from said natural gas; and further supplying said natural gas from said outlet separator means to said turboexpander means for further condensation of water vapor remaining in said natural gas, said flow of natural gas from said outlet separator means to said turboexpander means being controlled by valve means responsive to the water vapor content of said natural gas output of said outlet separator means.

14. The method for dehydration of well head natural gas according to claim 8, further including generating electrical energy by coupling a generator means through reduction gears to said turboexpander means.

* * * * *